(12) United States Patent
Baig et al.

(10) Patent No.: US 10,258,549 B2
(45) Date of Patent: Apr. 16, 2019

(54) METHOD OF PROTECTING TEETH AGAINST EROSION

(71) Applicant: The Procter & Gamble Company, Cincinnati, OH (US)

(72) Inventors: Arif Ali Baig, Mason, OH (US); Robert Vincent Faller, Loveland, OH (US); Donald James White, Jr., Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/268,692

(22) Filed: Sep. 19, 2016

(65) Prior Publication Data

US 2017/0007514 A1 Jan. 12, 2017

Related U.S. Application Data

(63) Continuation of application No. 10/737,425, filed on Dec. 16, 2003, now abandoned, which is a continuation-in-part of application No. 10/319,108, filed on Dec. 13, 2002, now Pat. No. 6,685,920, which is a continuation-in-part of application No. 09/710,250, filed on Nov. 10, 2000, now Pat. No. 6,713,049.

(60) Provisional application No. 60/165,351, filed on Nov. 12, 1999.

(51) Int. Cl.
| | |
|---|---|
| *A61K 8/21* | (2006.01) |
| *A23G 4/06* | (2006.01) |
| *A23G 4/08* | (2006.01) |
| *A23G 4/12* | (2006.01) |
| *A61K 8/19* | (2006.01) |
| *A61K 8/24* | (2006.01) |
| *A61K 8/81* | (2006.01) |
| *A61Q 11/00* | (2006.01) |
| *A61K 6/00* | (2006.01) |
| *A61K 8/20* | (2006.01) |
| *A61K 8/25* | (2006.01) |
| *A61K 8/29* | (2006.01) |
| *A61K 8/34* | (2006.01) |
| *A61K 8/365* | (2006.01) |
| *A61K 8/46* | (2006.01) |
| *A61K 8/73* | (2006.01) |

(52) U.S. Cl.
CPC ............... *A61K 8/21* (2013.01); *A23G 4/06* (2013.01); *A23G 4/08* (2013.01); *A23G 4/126* (2013.01); *A61K 6/0017* (2013.01); *A61K 8/19* (2013.01); *A61K 8/20* (2013.01); *A61K 8/24* (2013.01); *A61K 8/25* (2013.01); *A61K 8/29* (2013.01); *A61K 8/345* (2013.01); *A61K 8/365* (2013.01); *A61K 8/463* (2013.01); *A61K 8/73* (2013.01); *A61K 8/731* (2013.01); *A61K 8/81* (2013.01); *A61K 8/8147* (2013.01); *A61Q 11/00* (2013.01); *A61K 2800/28* (2013.01); *A61K 2800/48* (2013.01); *A61K 2800/52* (2013.01); *A61K 2800/5424* (2013.01); *A61K 2800/92* (2013.01)

(58) Field of Classification Search
CPC ........................................................ A61K 8/21
See application file for complete search history.

(56) References Cited

U.S. PATENT DOCUMENTS

| | | |
|---|---|---|
| 2,191,199 A | 2/1940 | Hall |
| 2,409,718 A | 10/1946 | Snell et al. |
| 2,498,344 A | 2/1950 | Rider et al. |
| 2,876,167 A | 3/1959 | Manahan |
| 2,946,725 A | 7/1960 | Norris |
| 3,004,897 A | 10/1961 | Shore |
| 3,105,796 A | 10/1963 | Holiday et al. |
| 3,105,798 A | 10/1963 | Holliday et al. |
| 3,130,002 A | 4/1964 | Fuchs et al. |
| 3,227,618 A | 1/1966 | Manahan et al. |
| 3,471,613 A | 10/1969 | Gagolski et al. |
| 3,562,385 A | 2/1971 | Block et al. |
| 3,634,585 A | 1/1972 | Manahan et al. |
| 3,862,307 A | 1/1975 | Di Giulio |
| 3,914,404 A | 10/1975 | Langer |
| 3,932,603 A | 1/1976 | Haas |
| 3,934,002 A | 1/1976 | Haefele |
| 3,956,480 A | 5/1976 | Dichter et al. |
| 3,959,458 A | 5/1976 | Agricola et al. |

(Continued)

FOREIGN PATENT DOCUMENTS

| | | |
|---|---|---|
| BE | 638645 A | 10/1963 |
| BE | 837701 A1 | 7/1976 |

(Continued)

OTHER PUBLICATIONS

Draus et al (Pyrophosphate and Hexametaphosphate Effects in Vitro Calculus Formation, Arch. Oral Biol., vol. 15, pp. 893-896, (1970)).*

(Continued)

*Primary Examiner* — Benjamin J Packard

(74) *Attorney, Agent, or Firm* — Parker D. McCrary; Alexandra S. Anoff; James E. Oehlenschlager

(57) ABSTRACT

Disclosed are methods of treating and protecting teeth against erosion by use of oral compositions comprising polymeric mineral surface active agents, metal ions such as stannous and zinc and combinations thereof. The present methods provide improved resistance of teeth to erosive demineralization or dissolution and prevention of tooth damage by subsequent exposure of teeth to erosive chemicals such as acidic foods and beverages.

20 Claims, No Drawings

(56) References Cited

U.S. PATENT DOCUMENTS

| | | |
|---|---|---|
| 4,048,300 A | 9/1977 | Tomlinson et al. |
| 4,051,234 A | 9/1977 | Gieske et al. |
| 4,138,477 A | 2/1979 | Gaffar |
| 4,206,215 A | 6/1980 | Bailey |
| 4,244,931 A | 1/1981 | Jarvis et al. |
| 4,247,526 A | 1/1981 | Jarvis et al. |
| 4,335,102 A | 6/1982 | Nakashima et al. |
| 4,340,583 A | 7/1982 | Wason |
| 4,357,318 A | 11/1982 | Shah et al. |
| 4,363,794 A | 12/1982 | Ochiai et al. |
| 4,370,314 A | 1/1983 | Gaffar |
| 4,443,197 A | 4/1984 | Fusayama et al. |
| 4,452,713 A | 6/1984 | Small |
| 4,459,281 A | 7/1984 | Sipos |
| 4,460,565 A | 7/1984 | Weststrate et al. |
| 4,515,772 A | 5/1985 | Parran, Jr. et al. |
| 4,526,181 A | 7/1985 | Heidjann et al. |
| 4,528,180 A | 7/1985 | Schaeffer |
| 4,528,181 A | 7/1985 | Heidjann et al. |
| 4,562,066 A | 12/1985 | Hayes et al. |
| 4,568,540 A | 2/1986 | Asano et al. |
| 4,612,384 A | 9/1986 | Omura et al. |
| 4,627,977 A | 12/1986 | Gaffar et al. |
| 4,664,906 A | 5/1987 | Sipos |
| 4,687,663 A | 8/1987 | Schaeffer |
| 4,749,758 A | 6/1988 | Dursch et al. |
| 4,795,628 A | 1/1989 | Afseth |
| 4,806,381 A | 2/1989 | Engelbrecht et al. |
| 4,842,847 A | 6/1989 | Amjad |
| 4,849,213 A | 7/1989 | Schaeffer |
| 4,853,237 A | 8/1989 | Prinkkila et al. |
| 4,853,247 A | 8/1989 | Barcelon et al. |
| 4,869,898 A | 9/1989 | Gaffar et al. |
| 4,877,603 A | 10/1989 | Degenhardt et al. |
| 4,892,725 A | 1/1990 | Amjad |
| 4,894,220 A | 1/1990 | Nabi et al. |
| 4,906,456 A | 3/1990 | Gaffar et al. |
| 4,913,895 A | 4/1990 | Miyake et al. |
| 4,939,284 A | 7/1990 | Degenhardt |
| 4,945,087 A | 7/1990 | Talwar et al. |
| 4,980,152 A | 12/1990 | Frazier et al. |
| 5,000,944 A | 3/1991 | Prencipe et al. |
| 5,004,597 A | 4/1991 | Majeti et al. |
| 5,009,882 A | 4/1991 | Degenhardt et al. |
| 5,011,913 A | 4/1991 | Benedict et al. |
| 5,013,541 A | 5/1991 | Elliott et al. |
| 5,015,466 A | 5/1991 | Parran, Jr. et al. |
| 5,017,363 A | 5/1991 | Suhonen |
| 5,032,386 A | 7/1991 | Gaffar et al. |
| 5,041,280 A | 8/1991 | Smigel |
| 5,049,375 A | 9/1991 | Tsujita et al. |
| 5,093,170 A | 3/1992 | Degenhardt et al. |
| 5,094,844 A | 3/1992 | Gaffar et al. |
| 5,096,701 A | 3/1992 | White, Jr. et al. |
| 5,098,711 A | 3/1992 | Hill et al. |
| 5,108,761 A | 4/1992 | Andon et al. |
| 5,130,123 A | 7/1992 | Reynolds et al. |
| 5,130,146 A | 7/1992 | Tsujita et al. |
| 5,145,666 A | 9/1992 | Lukacovic et al. |
| 5,176,900 A * | 1/1993 | White, Jr. ............ A61Q 11/00 424/49 |
| 5,192,532 A | 3/1993 | Guay et al. |
| 5,213,789 A | 5/1993 | Degenhardt et al. |
| 5,213,790 A | 5/1993 | Lukacovic et al. |
| 5,256,402 A | 10/1993 | Prencipe et al. |
| 5,281,410 A | 1/1994 | Lukacovic et al. |
| 5,281,411 A | 1/1994 | Majeti et al. |
| 5,292,501 A | 3/1994 | Degenhardt et al. |
| 5,296,214 A | 3/1994 | Gaffar |
| 5,296,215 A | 3/1994 | Burke et al. |
| 5,296,217 A | 3/1994 | Stookey |
| 5,320,831 A | 6/1994 | Majeti et al. |
| 5,320,832 A | 6/1994 | Catiis et al. |
| 5,338,537 A | 8/1994 | White, Jr. et al. |
| 5,368,844 A | 11/1994 | Gaffar et al. |
| 5,372,802 A | 12/1994 | Barrows et al. |
| 5,451,401 A | 9/1995 | Zerby et al. |
| 5,496,540 A | 3/1996 | Gaffar et al. |
| 5,565,190 A | 10/1996 | Santalucia et al. |
| 5,571,501 A | 11/1996 | Toy |
| 5,578,293 A | 11/1996 | Prencipe et al. |
| 5,589,160 A | 12/1996 | Rice |
| 5,599,525 A | 2/1997 | Hsu et al. |
| 5,601,803 A | 2/1997 | Masters et al. |
| 5,603,920 A | 2/1997 | Rice |
| 5,614,174 A | 3/1997 | Hsu et al. |
| 5,616,313 A | 4/1997 | Williams et al. |
| 5,630,999 A | 5/1997 | Burke et al. |
| 5,632,972 A | 5/1997 | Williams et al. |
| 5,648,064 A | 7/1997 | Gaffar et al. |
| 5,651,958 A | 7/1997 | Rice |
| 5,658,553 A | 8/1997 | Rice |
| 5,716,600 A | 2/1998 | Zahradnik et al. |
| 5,716,601 A | 2/1998 | Rice |
| 5,780,015 A | 7/1998 | Fisher et al. |
| 5,814,303 A | 9/1998 | Williams et al. |
| 5,820,854 A | 10/1998 | Glandorf |
| 5,833,952 A | 11/1998 | Grigor et al. |
| 5,885,553 A | 3/1999 | Michael |
| 5,885,554 A | 3/1999 | Michael et al. |
| 5,891,448 A | 4/1999 | Chow et al. |
| 5,902,568 A | 5/1999 | Ryles et al. |
| 5,939,052 A | 8/1999 | White, Jr. et al. |
| 5,945,088 A | 8/1999 | Delli Santi et al. |
| 5,948,390 A | 9/1999 | Nelson et al. |
| 5,980,776 A | 11/1999 | Zakikhani et al. |
| 6,071,434 A | 6/2000 | Davis et al. |
| 6,187,295 B1 | 2/2001 | Glandorf |
| 6,190,644 B1 | 2/2001 | McClanahan et al. |
| 6,241,972 B1 | 6/2001 | Herms et al. |
| 6,319,490 B1 | 11/2001 | Parker |
| 6,350,436 B1 | 2/2002 | Glandorf et al. |
| 6,383,473 B1 | 5/2002 | Parker |
| 6,555,094 B1 | 4/2003 | Glandorf et al. |
| 6,685,920 B2 | 2/2004 | Baig et al. |
| 6,713,049 B1 | 3/2004 | White, Jr. et al. |
| 6,821,507 B2 | 11/2004 | Glandorf et al. |
| 7,387,774 B2 | 6/2008 | Faller et al. |
| 2003/0165442 A1 | 9/2003 | Baig et al. |
| 2004/0146466 A1 | 7/2004 | Baig et al. |

FOREIGN PATENT DOCUMENTS

| | | |
|---|---|---|
| CA | 570803 A | 2/1959 |
| CA | 1018393 | 4/1974 |
| EP | 0026539 A2 | 4/1981 |
| GB | 490384 | 8/1938 |
| GB | 1290724 | 9/1972 |
| JP | 62019506 | 1/1987 |
| JP | 2001158725 | 6/2001 |
| WO | WO1994014406 A1 | 7/1994 |
| WO | WO1994014407 A1 | 7/1994 |
| WO | WO1995009603 A1 | 4/1995 |
| WO | WO1997030601 A1 | 8/1997 |
| WO | WO1997046462 A1 | 12/1997 |
| WO | WO1998004234 A1 | 2/1998 |
| WO | WO1998047475 A1 | 10/1998 |
| WO | WO1998051271 A1 | 11/1998 |
| WO | WO1999008550 A1 | 2/1999 |
| WO | WO1999020238 A1 | 4/1999 |
| WO | WO1999053893 A1 | 10/1999 |
| WO | WO2000013531 A2 | 3/2000 |
| WO | WO200134107 A1 | 5/2001 |
| WO | WO2001034108 A1 | 5/2001 |
| WO | WO2001052796 A2 | 7/2001 |
| WO | WO2001072144 A1 | 10/2001 |

OTHER PUBLICATIONS

Bartels et al., "The adsorption of two polyphosphonates on hydroxyapatite and their influence on the acid solubility of whole bovine enamel", Journal of Dentistry, n, No. 3, 1979, pp. 221-229.

(56) References Cited

OTHER PUBLICATIONS

Draus et al., "Pyrophosphate and Hexametaphosphate Effects in In Vitro Calculus Formation", Archs oral Biol. vol. 15, pp. 893-896, 1970.

Kerr et al., "Sodium Hexametaphosphate as an Aid in the Treatment of Periodontal Disease", Journal of Dentistry, 23:313-316 (1944).

Opinion, Ex Parte Novitski, U.S. Patent and Trademark, Board of Patent Appeals and Interferences, Decided Jan. 22, 1993, No. 92-1680, USPQ2d 1389.

All Office Actions for U.S. Appl. No. 10/737,425, filed Dec. 16, 2003—Now Abandoned.

All Office Actions for U.S. Appl. No. 10/319,108, filed Dec. 13, 2002, now U.S. Pat. No. 6,685,920.

All Office Actions for U.S. Appl. No. 09/710,250, filed Nov. 10, 2000, now U.S. Pat. No. 6,713,049.

All Office Actions for U.S. Appl. No. 10/734,381, filed Dec. 12, 2003, now U.S. Pat. No. 7,387,774.

\* cited by examiner

METHOD OF PROTECTING TEETH AGAINST EROSION

FIELD OF THE INVENTION

The present invention relates to methods of treating and protecting teeth against erosion by use of oral compositions comprising polymeric mineral surface active agents, metal ions such as stannous and zinc and combinations thereof. The present methods provide improved resistance of teeth to erosive demineralization or dissolution and prevention of tooth damage by subsequent exposure of teeth to erosive chemicals such as acidic foods and beverages.

BACKGROUND OF THE INVENTION

Oral care products such as toothpastes are routinely used by consumers as part of their oral care hygiene regimens. It is well known that oral care products can provide both therapeutic and cosmetic hygiene benefits to consumers. Therapeutic benefits include caries prevention which is typically delivered through the use of various fluoride salts; gingivitis prevention by the use of an antimicrobial agent such as triclosan, stannous fluoride, zinc citrate or essential oils; or hypersensitivity control through the use of ingredients such as strontium chloride or potassium nitrate. Cosmetic benefits provided by oral products include the control of plaque and calculus formation, removal and prevention of tooth stain, tooth whitening, breath freshening, and overall improvements in mouth feel impression which can be broadly characterized as mouth feel aesthetics.

In addition to the above mentioned therapeutic and cosmetic benefits oral care products can be used as a vehicle to deliver other benefits. The present inventors have surprisingly discovered additional important benefits of oral compositions comprising certain chemical agents that have affinity for the tooth surface. These agents either bind to the tooth surface or form insoluble compounds or complexes on the tooth surface, thereby forming a protective film or coating on the tooth surface. As a result of these protective coatings, teeth are provided with remarkable resistance and protection against dental erosion challenges for extended periods of time following use of the composition containing these agents.

Dental erosion is a permanent loss of tooth substance from the surface by the action of chemicals, such as harsh abrasives and acids, as opposed to subsurface demineralization or caries caused by bacterial action. Dental erosion is a condition that does not involve plaque bacteria and is therefore distinct from dental caries, which is a disease caused by acids generated by plaque bacteria. Dental erosion may be caused by extrinsic or intrinsic factors. Extrinsic erosion is the result of oral consumption of dietary acids such as acidic beverages or fruit juices and environmental factors such as exposure to airborne contamination or acidic water in swimming pools. Intrinsic erosion is caused for example by endogeous acids produced in the stomach and which contact the teeth during the processes of vomiting, regurgitation or reflux. The main cause of regurgitation and induced vomiting are eating disorder conditions such as nervous vomiting, anorexia or bulimia (Moss, 1998, *Int. Den. J.*, 48, 529).

The incidence and severity of dental erosion is on the rise with the increase in the consumption of acidic beverages and juices. The pH and titratable acidity of acidic beverages have been identified as the main causative agents in the initiation and progression of dental erosion (Lussi, 1995, *Caries Res.* 29, 349). Thus methods have been disclosed to modify acidic food and beverage products in order to prevent their erosive effect on teeth. See for example, U.S. Pat. No. 5,108,761 and WO 01/52796 both assigned to The Procter & Gamble Company; U.S. Pat. Nos. 6,383,473; 6,319,490; WO 01/72144; and WO 00/13531 all assigned to SmithKline Beecham; CA 1018393 assigned to General Foods Corporation; U.S. Pat. No. 3,471,613 and BE 638645, both assigned to Colonial Sugar Refining Co; and U.S. Pat. No. 4,853,237 assigned to Sinebrychoff Oy. In addition there have been disclosures of oral care compositions comprising agents indicated to provide teeth with antierosion or acid resistance benefits. See for example, JP 2001/158725; U.S. Pat. Nos. 4,363,794 and 4,335,102 all assigned to Lion Corporation; U.S. Pat. No. 5,130,123 assigned to The University of Melbourne; WO 99/08550 and WO 97/30601 both assigned to SmithKline Beecham; U.S. Pat. No. 3,914,404, assigned to Dow Chemical Co.; and U.S. Pat. No. 3,105,798, assigned to The Procter & Gamble Co.

Because of the nearly epidemic incidence of dental erosion problems, there is a continuing need for improved products that provide immediate as well as sustained protection against dental erosion challenges. The present inventors have discovered that such immediate and sustained protection can be provided by the use of oral care products comprising polymeric mineral surface active agents such as polyphosphates that bind to teeth, or metal ions such as stannous, zinc or copper that form insoluble compounds that deposit onto teeth, and combinations thereof. The polymeric coating or insoluble precipitate deposited onto teeth act as a protective layer that prevents erosive chemicals from contacting the tooth surface and etching away tooth hard tissue.

SUMMARY OF THE INVENTION

The present invention relates to a method of protecting a subject's teeth from erosion caused by the action of chemicals, such as harsh abrasives and acids, by the use of an oral care composition comprising a polymeric mineral surface-active agent selected from the group consisting of condensed phosphorylated polymers; polyphosphonates; polycarboxylates and carboxy-substituted polymers; copolymers of phosphate- or phosphonate-containing monomers or polymers with ethylenically unsaturated monomers, amino acids, or with other polymers selected from proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) or poly(vinyl benzyl chloride); and mixtures thereof, wherein said polymeric mineral surface-active agent is substantive to teeth and deposits a layer that protects teeth from erosive damage. Advantageously, the antierosion protection is provided immediately after use of the present compositions and maintained for prolonged periods of time for at least about one hour thereafter. Also useful as antierosion agents are metal ions selected from stannous, zinc and copper, which deposit onto teeth a highly insoluble film or precipitate of compounds or complexes formed from the reaction of the metal ions with other ingredients of the oral composition and/or components of the enamel surface.

These and other features, aspects, and advantages of the present invention will become evident to those skilled in the art from the detailed description which follows.

DETAILED DESCRIPTION OF THE INVENTION

While the specification concludes with claims which particularly point out and distinctly claim the invention, it is believed the present invention will be better understood from the following description.

All documents cited are, in relevant part, incorporated herein by reference; the citation of any document is not to be construed as an admission that it is prior art with respect to the present invention.

All percentages and ratios used herein are by weight of the specific oral composition and not of the overall oral formulation that is delivered, unless otherwise specified. All measurements are made at 25° C., unless otherwise specified.

Herein, "comprising" means that other steps and other ingredients which do not affect the end result can be added. This term encompasses the terms "consisting of" and "consisting essentially of". By "oral composition" is meant a product which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition of the present invention may be in the form of a toothpaste, dentifrice, tooth powder, topical oral gel, mouthrinse, denture product, mouthspray, lozenge, oral tablet, or chewing gum.

The term "dentifrice", as used herein, means paste, gel, or liquid formulations unless otherwise specified. The dentifrice composition may be a single phase composition or may be a combination of two or more dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing the oral care compositions.

The term "teeth", as used herein, refers to natural teeth as well as artificial teeth or dental prosthesis.

The term "orally acceptable carrier" as used herein means any safe and effective materials for use in the compositions of the present invention. Such materials include fluoride ion sources, additional anticalculus agents, buffers, abrasive polishing materials, peroxide sources, alkali metal bicarbonate salts, thickening materials, humectants, water, surfactants, titanium dioxide, flavor system, sweetening agents, xylitol, coloring agents, and mixtures thereof.

Herein, the terms "tartar" and "calculus" are used interchangeably and refer to mineralized dental plaque deposits.

The present invention relates to use of oral compositions containing particular polymeric mineral surface active agents, metal ions selected from stannous, zinc and copper, and combinations thereof, which provide effective protection against dental erosion derived from the deposition on the tooth surface of a protective layer or coating comprised of the polymeric mineral surface active agent and/or a highly insoluble film or precipitate of compounds or complexes formed from the reaction of the metal ions with other ingredients of the oral composition and/or components of the enamel surface. Such insoluble compounds include the metal hydroxide, oxide, phosphate, fluorophosphate, oxyfluoride and the like. In particular, these agents provide physical (surface coverage) and/or chemical (insoluble compounds deposited on surface) control of tooth surface characteristics including modification of surface hydrophilic and hydrophobic properties and resistance to acid attack. Importantly, the protective effect is provided immediately after use of the oral composition and lasts for at least about an hour or longer.

The polymeric mineral surface active agents include any agent which will produce the desired surface protection effects. These agents also provide desired surface conditioning effects including: 1) the effective desorption of portions of undesirable adsorbed pellicle proteins, in particular those associated with tooth stain binding, calculus development and attraction of undesirable microbial species; 2) creating a hydrophilic tooth surface immediately after treatment; and 3) maintaining surface conditioning effects and control of pellicle film for extended periods following product use, including post brushing and throughout more extended periods. The effect of creating an increased hydrophilic surface can be measured in terms of a relative decrease in water contact angles. The hydrophilic surface, importantly, is maintained on the tooth surface for an extended period after using the product, e.g., tooth brushing. Many of these polymeric agents are also known or expected to provide tartar control or antistain/whitening or surface conditioning activities when applied in oral compositions, hence providing multiple clinical actions in improving the appearance of teeth, improving the tactile impression to consumers and maintaining the structure of the teeth.

The polymeric mineral surface active agents include any agent which will have a strong affinity for enamel surface, deposit a polymer layer or coating on the enamel surface and produce the desired surface protection effects. Suitable examples of such polymers are polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); polycarboxylates and carboxy-substituted polymers; and mixtures thereof. Suitable polymeric mineral surface active agents include the carboxy-substituted alcohol polymers described in U.S. Pat. Nos. 5,292,501; 5,213,789, 5,093,170; 5,009,882; and 4,939,284; all to Degenhardt et al.; the diphosphonate-derivatized polymers in U.S. Pat. No. 5,011,913 to Benedict et al.; and the synthetic anionic polymers including polyacrylates and copolymers of maleic anhydride or acid and methyl vinyl ether (e.g., Gantrez), as described, for example, in U.S. Pat. No. 4,627,977, to Gaffar et al. A preferred polymer is diphosphonate modified polyacrylic acid. Polymers with activity must have sufficient surface binding propensity to desorb pellicle proteins and remain affixed to enamel surfaces. For tooth surfaces, polymers with end or side chain phosphate or phosphonate functions may both be preferred although other polymers with mineral binding activity may prove effective depending upon adsorption affinity.

Additional examples of suitable phosphonate containing polymeric mineral surface active agents include the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakikhani et al. and U.S. Pat. No. 6,071,434 to Davis et al. Preferred polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other preferred polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsatd. C=C bonds (e.g., acrylate and methacrylate monomers), such as those having the following structure:

1. Co-telomer of acrylic acid and 2-(hydroxyphosphinyl)ethylidene-1,1-diphosphonic acid with structure:

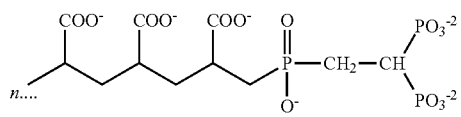

2. Co-polymer of acrylic acid and vinyldiphosphonic acid with structure:

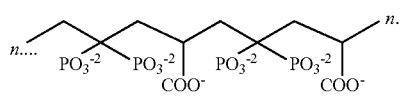

Suitable polymers include the diphosphonate/acrylate polymers supplied by Rhodia under the designation ITC 1087 (Average MW 3000-60,000) and Polymer 1154 (Average MW 6000-55,000).

A preferred polymeric mineral surface active agent will be stable with other components of the oral care composition such as ionic fluoride and metal ions and will not hydrolyze in high water content formulations, thus permitting a simple single phase dentifrice or mouthrinse formulation. If the polymeric mineral surface active agent does not have these stability properties, one option is a dual phase formulation with the polymeric mineral surface active agent separated from the fluoride or other incompatible component. Another option is to formulate a non-aqueous, essentially non-aqueous or limited water compositions to minimize reaction between the polymeric mineral surface active agent and other components.

A preferred polymeric mineral surface active agent is a polyphosphate. A polyphosphate is generally understood to consist of two or more phosphate molecules arranged primarily in a linear configuration, although some cyclic derivatives may be present. Although pyrophosphates are technically polyphosphates, the polyphosphates desired are those having around three or more phosphate molecules so that surface adsorption at effective concentrations produces sufficient non-bound phosphate functions, which enhance the anionic surface charge as well as hydrophilic character of the surfaces. The pyrophosphates are discussed separately under additional anticalculus agents. The inorganic polyphosphate salts desired include tripolyphosphate, tetrapolyphosphate and hexametaphosphate, among others. Polyphosphates larger than tetrapolyphosphate usually occur as amorphous glassy materials. Preferred in this invention are the linear "glassy" polyphosphates having the formula:

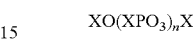

wherein X is sodium or potassium and n averages from about 3 to about 125. Preferred polyphosphates are those having n averaging from about 6 to about 21, such as those manufactured by FMC Corporation and commercially known as Sodaphos (n≈6), Hexaphos (n≈13), and Glass H (n≈21). A particularly preferred polyphosphate has n averaging about 21 such as Glass H. These polyphosphates may be used alone or in a combination thereof.

Oral compositions which comprise polyphosphates are disclosed in e.g., U.S. Pat. Nos. 5,939,052, 6,190,644, 6,187,295, and 6,350,436, all assigned to The Procter & Gamble Co. In these compositions, the polyphosphates are disclosed to provide benefits including tartar inhibition and reducing aesthetic negatives such as astringency and staining caused by other actives such as stannous. The use of polyphosphates for the prevention of dental erosion is not disclosed. The polyphosphate sources are also described in more detail in Kirk-Othmer *Encyclopedia of Chemical Technology*, Fourth Edition, Volume 18, Wiley-Interscience Publishers (1996).

The amount of polymeric mineral surface agent required is an effective amount to provide the protection from erosion due to acid or abrasive challenges, the protection lasting for at least about an hour after use of the composition. An effective amount of a polymeric mineral surface active agent will typically be from about 1% to about 35%, preferably from about 2% to about 30%, more preferably from about 5% to about 25%, and most preferably from about 6% to about 20%, by weight of the total oral composition.

The metal ions suitable for use in the present invention have strong affinity for enamel surface and include stannous, copper and zinc ions. These ions provide surface protection effects by reacting with tooth surface ions and/or other components of the composition to produce highly insoluble compounds on the surface. Additionally, these metal ions undergo oxidation and hydrolysis under salivary pH conditions and produce insoluble deposits on tooth surfaces.

The present compositions may comprise a metal ion source that provides stannous ions, zinc ions, copper ions, or mixtures thereof. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper.

Stannous, zinc and copper ions are derived from the metal ion source(s) found in the dentifrice composition in an effective amount to provide the antierosion benefit or other benefits. Stannous, zinc and copper ions have been found to help in the reduction of gingivitis, plaque, sensitivity, and improved breath benefits. An effective amount is defined as from at least about 500 ppm to about 20,000 ppm metal ion of the total composition, preferably from about 2,000 ppm to about 15,000 ppm. More preferably, metal ions are present in an amount from about 3,000 ppm to about 13,000 ppm and even more preferably from about 5,000 ppm to about 10,000 ppm. This is the total amount of metal ions (stannous, zinc, copper and mixtures thereof) that is present in the compositions for delivery to the tooth surface.

Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients needed to stabilize the stannous may also be included, such as the ingredients described in Majeti et al. and Prencipe et al. However, it has been found that the antierosion benefits of stannous may be negatively affected by certain stabilizing agents, such as phytic acid, ethylenediaminetetraacetic acid (EDTA) and salts thereof. The present compositions are thus preferably essentially free of phytates and ethylenediaminetetraacetates. By "essentially free" is meant that the compositions have no more than 0.01% by weight of these agents.

The preferred stannous salts are stannous fluoride and stannous chloride dihydrate. Other suitable stannous salts include stannous acetate, stannous tartrate and sodium stannous citrate. Examples of suitable zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880. Zinc citrate and zinc lactate are particularly preferred. Examples of suitable copper ion sources are listed in U.S. Pat. No. 5,534,243. The combined metal ion source(s) will be present in an amount of from about 0.1% to about 11%, by weight of the final composition. Preferably, the metal ion sources are present in an amount of from about 0.5 to about 7%, more preferably from about 1% to about 5%. Preferably, the stannous salts may be present in an amount of from about 0.1 to about 7%, more preferably from about 1% to about 5%, and most preferably from about 1.5% to about 3% by weight of the total composition. The amount of zinc or copper salts used in the present invention ranges from about 0.01 to about 5%, preferably from about 0.05 to about 4% and more preferably from about 0.1 to about 3.0%.

In preparing the present compositions, it is desirable to add one or more aqueous carriers to the compositions. Such materials are well known in the art and are readily chosen by one skilled in the art based on the physical and aesthetic properties desired for the compositions being prepared. These carriers may be included at levels which do not interfere or prohibit the surface effects of the polymeric mineral surface active agent. The amount of polymeric mineral surface active agent may be increased to account for the additional carriers. Aqueous carriers typically comprise from about 50% to about 99%, preferably from about 70% to about 98%, and more preferably from about 80% to about 95%, by weight of the oral composition.

The oral composition of the present invention may incorporate a soluble fluoride source capable of providing free fluoride ions. The fluoride ion source may preferably be in a separate phase than the polymeric surface active agent to aid in stability. Preferred soluble fluoride ion sources include sodium fluoride, stannous fluoride, indium fluoride, amine fluoride and sodium monofluorophosphate. Sodium fluoride and stannous fluoride the most preferred soluble fluoride ion source. Stannous fluoride and methods of stabilization are described in U.S. Pat. No. 5,004,597 issued to Majeti et al. and in U.S. Pat. No. 5,578,293 issued to Prencipe et al., in addition to other sources Norris et al., U.S. Pat. No. 2,946,725, issued Jul. 26, 1960, and Widder et al., U.S. Pat. No. 3,678,154 issued Jul. 18, 1972, disclose such fluoride ion sources as well as others.

The present compositions contain a soluble fluoride ion source capable of providing from about 50 ppm to about 3500 ppm, and preferably from about 500 ppm to about 3000 ppm of free fluoride ions.

The present compositions may contain a buffering agent. Buffering agents, as used herein, refer to agents that can be used to adjust the pH of the compositions to a range of about pH 4 to about pH 10. The oral composition containing a polymeric mineral surface active agent will typically have a slurry pH of from about 4 to about 10, preferably from about 4.5 to about 8, and more preferably from about 5.5 to about 7. The buffering agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 1% to about 10%, and more preferably from about 1.5% to about 3%, by weight of the present composition.

Optional agents that may be used in combination with the polymeric mineral surface active agent include such materials known to be effective in reducing calcium phosphate mineral deposition related to calculus formation. Pyrophosphate salts may be used in the present invention as anticalculus agents or as buffering agents, as long of the surface conditioning effects of the polymeric surface active agent is not eliminated. The pyrophosphate salts useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%, by weight of the composition. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 2.5% to about 8%, by weight of the composition. Some or all of the tetrasodium pyrophosphate may be undissolved in the product and present as tetrasodium pyrophosphate particles. Pyrophosphate ions in different protonated states (e.g., $HP_2O_7^{-3}$) may also exist depending upon the pH of the composition and if part of the tetrasodium pyrophosphate is dissolved.

Compositions may also comprise a mixture of dissolved and undissolved pyrophosphate salts. Any of the above mentioned pyrophosphate salts may be used.

The pyrophosphate salts are described in more detail in Kirk-Othmer *Encyclopedia of Chemical Technology*, Third Edition, Volume 17, Wiley-Interscience Publishers (1982). Additional anticalculus agents include other materials known to be effective in reducing calcium phosphate mineral deposition related to calculus formation. Agents included are synthetic anionic polymers including polyacrylates and copolymers of maleic anhydride or acid and methyl vinyl ether (e.g., Gantrez), as described, for example, in U.S. Pat. No. 4,627,977, to Gaffar et al., as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof.

An abrasive polishing material may also be included in the oral compositions. The abrasive polishing material contemplated for use in the compositions of the present invention can be any material which does not excessively abrade dentin. The abrasive polishing material should be formulated in the oral composition so that it does not compromise the stability of any ingredients, such as stannous fluoride. Typical abrasive polishing materials include silica gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982. Silica abrasives are also described in Rice, U.S. Pat. Nos. 5,589,160; 5,603,920; 5,651,958; 5,658,553; and 5,716,601. The abrasive in the toothpaste compositions described herein is generally present at a level of from about 6% to about 70% by weight of the composition. Preferably, toothpastes contain from about 10% to about 50% of abrasive, by weight of the dentifrice composition.

The present invention may include a peroxide source in the oral composition. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the dentifrice composition.

The present invention provides compositions in the form of toothpastes, dentifrices, tooth powder, topical oral gels, mouthrinses, denture product, mouthsprays, lozenges, oral tablets, and chewing gums. Typically these compositions will contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the dentifrice composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. The humectant generally comprises from about 0% to 70%, and preferably from about 15% to 55%, by weight of the composition.

Water employed in the preparation of commercially suitable oral compositions should preferably be of low ion content and free of organic impurities. Water will generally comprise from about 5% to about 70%, and preferably from about 10% to about 50%, by weight of the composition herein. The polymeric mineral surface active agent may require a lower level of water to be stable. Generally, the level of water is up to about 20%, preferably from about 5% to about 14%, and more preferably from about 7% to about 12%, by weight of the oral composition. The amounts of water include the free water which is added plus that which is introduced with other materials, such as with sorbitol, silica, surfactant solutions, and/or color solutions.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the para-menthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

The present invention may also include xylitol. Xylitol is a sugar alcohol that is used as a sweetener and humectant. Xylitol may provide a therapeutic effect, such as an antibacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the total composition. Alternatively, if xylitol is used as a sweetener, it may be present at a lower level, such as from about 0.005% to about 5%, by weight of the dentifrice composition.

Sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1, 3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis [4-(R-amino)-1-pyridinium] alkanes as disclosed in U.S. Pat. No. 4,206,215, issued Jun. 3, 1980, to Bailey. Other antimicrobials such as copper bisglycinate, copper glysinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. The water insoluble antimicrobial agents, water soluble agents, and enzymes may be present in either the first or second dentifrice compositions. The quaternary ammonium agents, stannous salts, and substituted guanidines are preferably present in an oral composition separate from the polymeric mineral surface active agent. These agents may be present at levels of from about 0.01% to about 1.5%, by weight of the dentifrice composition.

The oral compositions of the present invention are in the form of toothpastes, dentifrices, topical oral gels, mouthrinses, denture products, mouthsprays, lozenges, oral tablets, or chewing gums. The dentifrice compositions may be a paste, gel, or any configuration or combination thereof. If a dual phase formulation is used, it is preferred that the dentifrice compositions be physically separated. Also for aesthetics reasons, it is preferred that one composition be a paste and the other composition be a gel. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. No. 4,687,663, issued Aug. 18, 1987; and U.S. Pat. No. 4,849,213, issued Jul. 18, 1989, all to Shaeffer. The dispenser will deliver approximately equal amounts of each dentifrice composition through an opening. The compositions may intermix once dispensed. Alternatively, the oral formulation may be delivered from a kit containing two separate dispensers which are used to deliver two dentifrice compositions that are both used simultaneously.

The method of use for providing immediate and sustained protection against dental erosion herein comprises contacting a subject's dental enamel surfaces and mucosa in the mouth with the oral compositions according to the present invention. The method of use may be by brushing with a dentifrice or rinsing with a dentifrice slurry or mouthrinse. Other methods include contacting the topical oral gel, dentures product, mouthspray, or other form with the subject's teeth and oral mucosa. The subject may be any person or lower animal whose tooth surface contact the oral composition.

It should be understood that the present invention relates not only to methods for delivering the present active agents containing compositions to the oral cavity of a human, but also to methods of delivering these compositions to the oral cavity of other animals, e.g., household pets or other domestic animals, or animals kept in captivity.

For example, a method of use may include a person brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions. The composition including the polymeric surface active agent is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Example 1

The effectiveness of dentifrice compositions of the present invention were tested according to the following in vitro erosion cycling protocol.

Tooth (dentin or enamel) specimens are prepared by cutting 3 mm 4 mm cores from extracted, human teeth using a diamond core drill. The teeth, collected by local surgeons, are stored until use in a 5% Thymol solution maintained at room temperature. Specimens are mounted on lucite rods with a dental acrylic (Dura Base, Reliance Mfg. Co.) covering all sides except the surface. Course polishing with 600-grit silicon carbide-water slurry is used to remove approximately 50 microns of the outer specimen surface to ensure homogeneity among specimens. Specimens are then polished with gamma alumina (Buehler No. 3, B Gamma Micropolish Alumina) to a mirror-like finish.

Portions of the surface of each specimen are then covered with an acid resistant nail polish (placed in a mesial-distal fashion), leaving at least one uncovered strip of tooth surface exposed for treatment. Covered portions remain covered with the acid-resistant nail polish throughout the experiment, serving as the control (untreated) areas for later microradiographic analysis.

After placing specimens in groups of four, each group of specimens is placed in 20 ml of fresh, pooled human saliva for at least one hour to form an initial layer of pellicle on the specimen surfaces prior to first day of treatment. Typical test products (dentifrice treatment A) are listed in Table 1 along with the acidic beverage (Coca Cola) challenge (Treatment B), though both the dentifrice treatments and challenge can be modified from study to study. Other acidic beverages used in similar studies include ginger ale, grapefruit juice, orange juice, etc. Dentifrice slurries are prepared by mixing 5 grams of dentifrice with 15 grams of fresh, pooled human saliva for a period of not less than 4 nor more than 5 minutes prior to use. A fresh slurry of dentifrice:saliva is prepared for each treatment. After treatment with the appropriate dentifrice slurry (1 minute exposure followed by brief rinsing with deionized, distilled water), specimens are exposed to the saliva bath for five minutes before immersing into the acidic beverage challenge (Treatment B) for ten minutes. Fresh beverage is used for each treatment. This series of treatments (A followed by saliva followed by B) is repeated 7 times a day for a total of five treatment days. A general protocol is presented in Table 2. After each treatment, each group of specimens is rinsed with deionized, distilled water and placed in approximately 20 ml of fresh, pooled human saliva until the time of the next treatment. At any time specimens are not in treatment, they are placed in 20 ml of fresh, pooled human saliva (stirred). The specimens remain in the saliva bath overnight (stirred at room temperature).

After 5 days of treatment, thin cross-sections (80-120 μm thick) of each specimen are removed for assessment using standardized transverse microradiography (TMR) techniques. The exposed, treated area of each specimen is assessed with respect to complete mineral loss (erosion). Results are presented in Table 3 as depth (in microns) of total mineral loss from the original specimen surface using the covered (untreated) areas as anatomical reference points.

The following example compositions were evaluated for their effect on protecting the teeth against the erosive challenge of a commercially available carbonated soft drink, Coca Cola.

TABLE 1

| Dentifrice Actives Treatment A | Acid Beverage Treatment B |
| --- | --- |
| Stannous + Polyphosphate[1] | Coca Cola |
| Zinc Lactate + Polyphosphate[1] | Coca Cola |
| Polyphosphate[1] | Coca Cola |
| Zinc Citrate + Polyphosphate[1] | Coca Cola |
| Zinc Citrate | Coca Cola |
| Placebo | Coca Cola |

[1]Polyphosphate is Glass H supplied by FMC Corp.

TABLE 2

| Day 1 | TIME | |
| --- | --- | --- |
| saliva soak(night before □12 hr) | | |
| treatment 1 | 8:00 am | |
| saliva soak | | |
| treatment 2 | 9:00 am | |
| saliva soak | | |
| treatment 3 | 10:00 am | |
| saliva soak | | |
| treatment 4 | 11:00 pm | |
| saliva soak | | Repeat for 5 days |
| treatment 5 | 1:00 pm | |
| saliva soak | | |
| treatment 6 | 2:00 pm | |
| saliva soak | | |
| treatment 7 | 3:00 pm | |
| saliva overnight | | |

TABLE 3

| Dentifrice Test Product Containing: | Depth of Complete Mineral Loss (μm) |
| --- | --- |
| Stannous + Polyphosphate[1] | 0 |
| Zinc Lactate + Polyphosphate[1] | 0 |
| Polyphosphate[1] | 1.7 |
| Zinc Citrate + Polyphosphate[1] | 4.0 |
| Zinc Citrate | 10.7 |
| Placebo | 13.9 |

[1]Polyphosphate is Glass H supplied by FMC Corp.

These data show that compared to no treatment, there is significantly less loss of tooth mineral surface when the tooth was treated with dentifrice compositions containing polyphosphate, stannous and zinc ion, with no loss at all when using the combination of polyphosphate with either zinc or stannous. These findings provide strong evidence of the protective nature of oral compositions containing polyphosphate, stannous or zinc either alone or in combination in their ability to protect human enamel against erosion from acidic challenge.

The sustained effects of Glass H polyphosphate in protecting the enamel surface against erosive challenges were tested in a separate study design wherein groups of specimens were challenged at intervals of 5 minutes, 1 hour or 2 hours post treatment in the dentifrice slurry with the acidic beverage (Coca Cola) challenge.

An example of the result of studies demonstrating the extended protection afforded the tooth specimens as a result of treatment with the dentifrice according to the present invention is included in Table 4, which presents data from a 6-leg study design.

TABLE 4

| | Depth of Complete Mineral Loss (μm) | | |
| --- | --- | --- | --- |
| Dentifrice Test Product Containing: | Challenged at 5 minutes post dentifrice treatment | Challenged at 1 hour post dentifrice treatment | Challenged at 2 hours post dentifrice treatment |
| Polyphosphate[1] | 0.0 | 0.0 | 0.0 |
| Control | 8.5 | 10.5 | 15.9 |

[1]Polyphosphate is Glass H supplied by FMC Corp.

Example II

| Ingredient | Formula A | Formula B | Formula C | Formula D | Formula E |
| --- | --- | --- | --- | --- | --- |
| Flavor | 1.000 | 1.200 | 1.500 | 1.150 | 0.800 |
| Glycerin | 53.166 | 54.300 | 52.872 | 9.000 | 38.519 |
| Poloxamer 407 | 5.000 | 3.000 | 8.000 | — | — |
| Stannous Chloride | 0.680 | — | — | — | — |
| Stannous Sulfate | — | 1.460 | — | — | — |
| Stannous Fluoride | 0.454 | — | — | — | 0.454 |
| Zinc Lactate Dihydrate | — | — | — | — | 2.500 |
| Sodium Fluoride | — | 0.320 | — | 0.243 | — |
| Sodium Monofluorophosphate | — | — | 1.128 | — | — |
| Sodium Lauryl Sulfate[(a)] | 7.500 | 6.000 | 4.000 | 4.000 | 2.500 |
| Silica | 20.000 | 18.000 | 22.000 | 22.000 | 25.000 |
| Carboxymethyl Cellulose | 0.200 | 0.200 | 0.400 | — | — |
| Sodium Gluconate | — | 1.470 | — | — | 0.652 |
| Sodium Saccharin | 0.400 | 0.350 | 0.500 | 0.460 | 0.500 |
| Titanium Dioxide | 0.500 | 0.500 | 0.500 | — | — |
| Xanthan Gum | 0.100 | 0.200 | 0.100 | 0.600 | 0.600 |
| Carageenan | — | — | — | — | 0.600 |
| Glass H Polyphosphate | 11.000 | 13.000 | 9.000 | — | 13.000 |
| Poly (diphosphonate/acrylate) | — | — | — | 5.000 | — |
| Na hydroxide[(b)] | — | — | — | trace | — |
| FD&C Blue #1[(c)] | — | — | — | — | 0.025 |
| Sorbitol[(d)] | — | — | — | 28.937 | — |
| Carbopol | — | — | — | 0.200 | — |

| Ingredient | Formula A | Formula B | Formula C | Formula D | Formula E |
|---|---|---|---|---|---|
| Polyethylene Glycol | — | — | — | 3.000 | 7.000 |
| Propylene Glycol | — | — | — | — | 7.000 |
| Trisodium Phosphate | — | — | — | — | 1.100 |
| Water | — | — | — | 25.410 | — |

(a) 27.9% solution
(b) 50% solution
(c) 1% solution
(d) 70% solution

Dentifrice compositions (Formula A-E) are prepared using conventional mixing techniques as follows. Add the glycerin or sorbitol and thickening agents to the main mix tank and mix until homogeneous. If applicable, add the sodium gluconate to the main mix tank and mix until homogeneous. Add the sodium lauryl sulfate solution and flavor to the main mix tank and mix until thickeners are hydrated/dissolved. Add the silica and titanium dioxide to the main mix tank and mix until homogeneous. Add metal and/or fluoride salts to the main mix tank and mix until homogeneous. Finally add the polymeric mineral surface active agent (Glass H or polyphosphonate) to the main mix tank. Mix until homogeneous.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of protecting a subject's teeth from erosion comprising depositing onto the subject's teeth a polymer layer or coating from a dentifrice composition wherein the dentifrice composition comprises:
   a. 0.1% to about 7%, by weight of the dentifrice, stannous fluoride;
   b. from about 1% to about 35%, by weight of the dentifrice, inorganic polyphosphate salt selected from the group consisting of tripolyphosphate, tetrapolyphosphate, hexametaphosphate, and combinations thereof;
   c. up to about 20%, by weight of the dentifrice, water;
   d. from about 6% to about 70%, by weight of the composition, abrasive polishing agent;
   e. a flavor system;
   f. from about 0.25% to about 6%, by weight of the dentifrice, an amphoteric surfactant comprising cocamidopropyl betaine.

2. The method of claim 1 wherein the dentifrice composition comprises from about 5% to about 25% of an inorganic polyphosphate salt.

3. The method of claim 1 wherein the inorganic polyphosphate salt comprises hexametaphosphate.

4. The method of claim 1 wherein the inorganic polyphosphate salt comprises tripolyphosphate.

5. The method of claim 1 wherein the dentifrice composition further comprises from about 0.1% to about 15%, by weight of the dentifrice, thickening agent selected from the group consisting of carboxyvinyl polymers, carrageenan, hydroxyethyl cellulose, sodium carboxymethylcellulose, sodium hydroxyethyl cellulose, gum karaya, xanthan gum, gum arabic, gum tragacanth, and combinations thereof.

6. The method of claim 5 wherein the thickening agent comprises a carboxyvinyl polymer.

7. The method of claim 5 wherein the thickening agent comprises xanthan gum.

8. The method of claim 1 wherein the dentifrice composition further comprises a humectant selected from the group consisting of glycerin, sorbitol, polyethylene glycol, propylene glycol, and combinations thereof.

9. The method of claim 8 wherein the humectant comprises from about 15% to 55% glycerin.

10. The method of claim 1 wherein the abrasive polishing agent comprises precipitated silica.

11. A method of protecting a subject's teeth from erosion comprising depositing onto the subject's teeth a polymer layer or coating from a dentifrice composition wherein the dentifrice composition comprises:
    a. 0.1% to about 7%, by weight of the dentifrice, stannous fluoride;
    b. from about 6% to about 20%, by weight of the dentifrice, inorganic polyphosphate salt selected from the group consisting of tripolyphosphate, tetrapolyphosphate, hexametaphosphate, and combinations thereof;
    c. from about 10% to about 50%, by weight of the composition, abrasive polishing agent comprising precipitated silica;
    d. from about 15% to about 55%, by weight of the composition, glycerin;
    e. from about 0.1% to about 15%, by weight of the dentifrice composition, a thickening agent selected from the group consisting of carboxyvinyl polymers, carrageenan, hydroxyethyl cellulose, sodium carboxymethylcellulose, sodium hydroxyethyl cellulose gum karaya, xanthan gum, gum arabic, gum tragacanth and combinations thereof;

f. up to about 20%, by weight of the dentifrice, water;

g. a flavor system;

h. from about 0.25% to about 6%, by weight of the dentifrice, an amphoteric surfactant comprising cocamidopropyl betaine.

12. The method of claim 11 wherein the thickening agent comprises a carboxyvinyl polymer.

13. The method of claim 12 wherein the thickening agent further comprises xanthan gum.

14. The method of claim 11 wherein the dentifrice further comprises from about 5% to about 14%, by weight of the composition, water.

15. The method of claim 11 wherein the dentifrice further comprises stannous chloride dihydrate.

16. The method of claim 11 wherein the dentifrice further comprises sodium gluconate.

17. The method of claim 11 wherein the dentifrice further comprises from about 0.25% to about 5%, by weight of the composition, titanium dioxide.

18. The method of claim 11 wherein the dentifrice further comprises sodium lauryl sulfate.

19. The method of claim 11, wherein the inorganic polyphosphate salt is tripolyphosphate.

20. The method of claim 19, wherein the dentifrice composition comprises no added water.

* * * * *